(12) United States Patent
Kesling

(10) Patent No.: US 6,217,322 B1
(45) Date of Patent: Apr. 17, 2001

(54) LOW FRICTION ORTHODONTIC APPLIANCE

(76) Inventor: Peter C. Kesling, 611 W. 250 South, LaPorte, IN (US) 46350

( * ) Notice: Subject to any disclaimer, the term of this patent is extended or adjusted under 35 U.S.C. 154(b) by 0 days.

(21) Appl. No.: 09/494,624

(22) Filed: Jan. 31, 2000

(51) Int. Cl.$^7$ .................................................. A61C 3/00
(52) U.S. Cl. ............................................................ 433/17
(58) Field of Search ................................. 433/17, 20, 10, 433/13

(56) References Cited

U.S. PATENT DOCUMENTS

| | | |
|---|---|---|
| 3,494,034 | 2/1970 | Kesling . |
| 3,526,961 | 9/1970 | Kesling . |
| 3,838,514 * | 10/1974 | Polak ...................................... 433/20 |
| 3,874,080 | 4/1975 | Wallshein . |
| 4,028,809 | 6/1977 | Wallshein . |
| 4,781,582 | 11/1988 | Kesling . |
| 4,963,092 * | 10/1990 | Snead ...................................... 433/17 |
| 5,057,012 | 10/1991 | Kesling . |
| 5,230,620 * | 7/1993 | Watanabe ............................... 433/17 |
| 5,292,248 * | 3/1994 | Schultz ................................... 433/17 |
| 5,356,288 * | 10/1994 | Cohen ..................................... 433/10 |
| 5,556,277 * | 9/1996 | Yawata et al. ......................... 433/17 |
| 5,727,941 | 3/1998 | Kesling . |
| 5,931,667 * | 8/1999 | Papandreas ............................. 433/17 |

* cited by examiner

Primary Examiner—Todd E. Manahan
(74) Attorney, Agent, or Firm—Lloyd L. Zickert

(57) ABSTRACT

A low friction orthodontic appliance in the form of a solid one-piece buccal tube or a convertible buccal tube, which includes a lumen having a close-fit control portion at one end for receiving torque forces from an archwire and a loose-fit relieved portion at the other end providing clearance between at least three sides of the archwire and the appliance to reduce sliding friction.

14 Claims, 2 Drawing Sheets

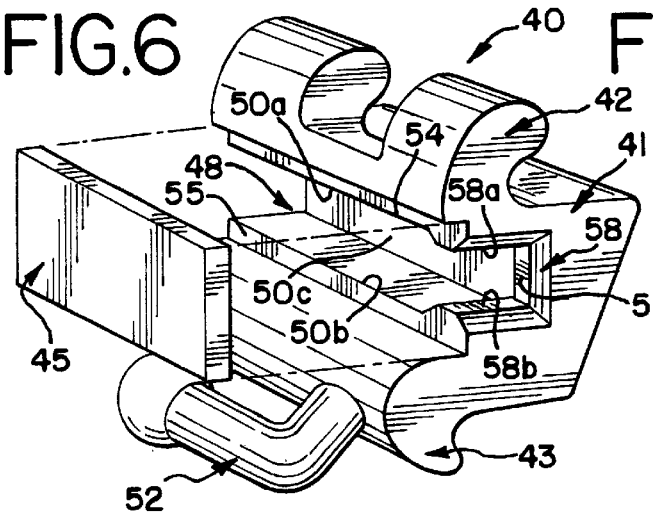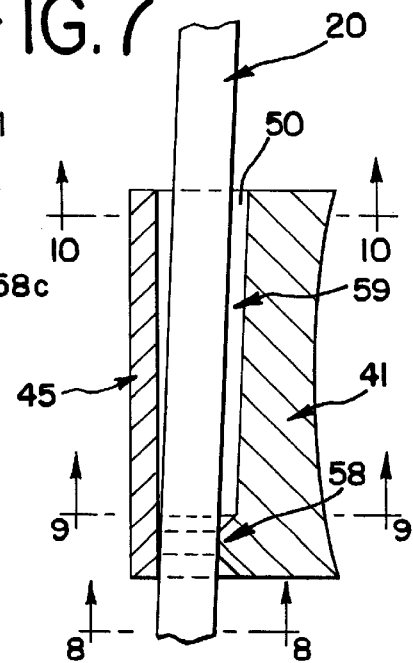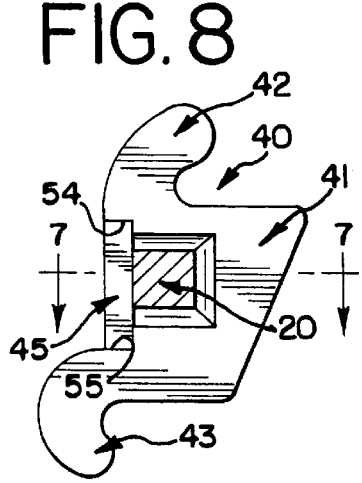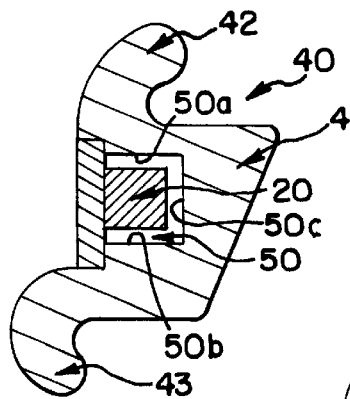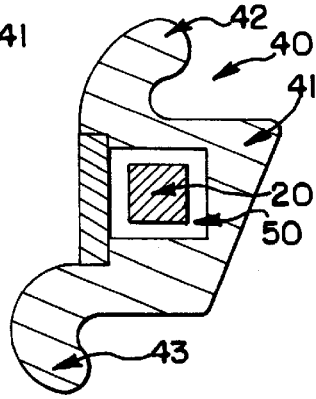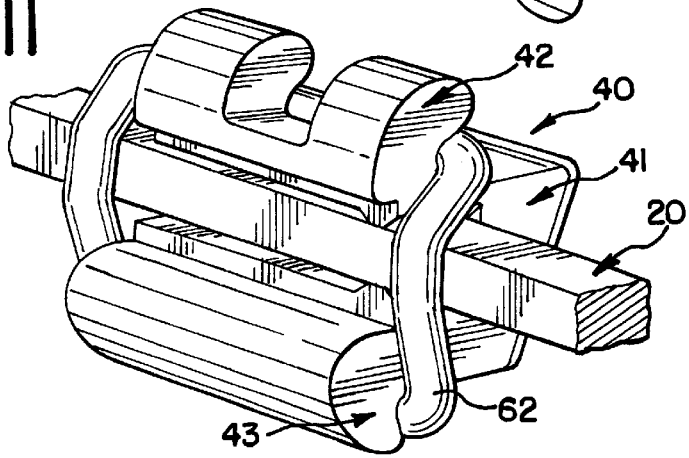

LOW FRICTION ORTHODONTIC APPLIANCE

DESCRIPTION

The present invention relates in general to an orthodontic appliance, and more particularly to a low friction orthodontic appliance in the form of a buccal tube or a convertible buccal tube, and still more particularly to an archwire appliance having a control portion for the application of torque and a relieved portion for reducing sliding friction.

BACKGROUND OF THE INVENTION

It is well known to provide buccal tubes for anchoring archwires and applying torque during orthodontic treatment. During orthodontic treatment an archwire will have sliding movement relative to the tubes.

Heretofore, it has also been known to provide rectangular archwire for effecting torque control between the archwire and the buccal tubes. Where torque was desired, the lumens in the tubes were configured such that the sliding friction between the archwire and the tubes could affect treatment time. Some heretofore known tubes that control torque and provide some relief around portions of the archwire include U.S. Pat. Nos. 4,781,582; 5,057,012, and 5,727,941. However, treatment time is at least partially dependent on the level of sliding friction between the archwire and the tubes. A lower level of sliding friction enhances and shortens the treatment time.

SUMMARY OF THE INVENTION

The improved tube of the present invention provides the maximum amount of reduced sliding friction between an archwire and a tube by providing a control portion for the archwire at one end of the tube and a relieved portion defining a relief around at least three sides of the archwire at the other end. The present invention is in providing a low friction orthodontic appliance of the present invention is in the form of a buccal tube or a convertible buccal tube wherein the lumen of the tube includes a control portion at one end capable of producing torquing forces and a relieved portion at the other end defining clearance along at least three sides of the archwire to reduce sliding friction. Preferably, the control portion will be at the mesial end of the tube (towards the front of the mouth), but it could be at the distal end thereof (toward the back of the mouth). In the form of a non-convertible buccal tube the relieved portion provides clearance about all surfaces and edges of the archwire and in the form of a convertible buccal tube at least three sides of the archwire. Thus, the sliding friction of torque-applying buccal tubes, either one-piece or convertible, is minimized by the present invention, thereby maximizing the treatment capability of the tube.

It is therefore an object of the present invention to provide a new and improved buccal tube for use in orthodontic treatment that reduces the sliding friction between the archwire and the tube.

A further object of the present invention is in the provision of an orthodontic appliance in the form of a buccal tube or a convertible buccal tube that reduces friction between the archwire and the tube, thereby maximizing the efficiency of the orthodontic treatment of a patient.

Another object of the present invention is to provide a low friction buccal tube having a torque control portion at one of the ends of the tube and a relieved portion at the other end of the tube to minimize the sliding friction between the archwire and the tube.

A still further object of the present invention is to provide a convertible buccal tube having a torque control portion at one end of the tube and a relieved portion at the other end of the tube providing clearance between at least three sides of the archwire and the appliance.

Other objects, features and advantages of the invention will be apparent from the following detailed disclosure, taken in conjunction with the accompanying sheets of drawings, wherein like reference numerals refer to like parts.

DESCRIPTION OF THE DRAWINGS

FIG. 6 is a perspective view of a modification of the invention where the appliance of the invention is a convertible buccal tube with the convertible cap removed and shown in exploded view to clearly illustrate the invention as a bracket with a horizontal facing archwire slot;

FIG. 7 is a longitudinal sectional view taken through the embodiment of FIG. 6 and substantially along line 7—7 of FIG. 8 and illustrating the archwire in top plan view and also having the lower tie wing removed for purposes of clarity;

FIG. 8 is a mesial end elevational view of the tube of FIGS. 6 and 7 and taken substantially in the direction of the arrows along line 8—8 of FIG. 7;

FIG. 9 is a transverse sectional view taken through the tube of FIGS. 6 and 7 and substantially along lines 9—9 of FIG. 7;

FIG. 10 is a transverse sectional view taken substantially along line 10—10 of FIG. 7; and FIG. 11 is a perspective view of an appliance in the form of a convertible tube like that in FIG. 6 without a hook and where the convertible cap has been removed so that the tube can function as a bracket and illustrating a ligature in place to retain the wire in the archwire slot.

DESCRIPTION OF THE INVENTION

Figure 1:
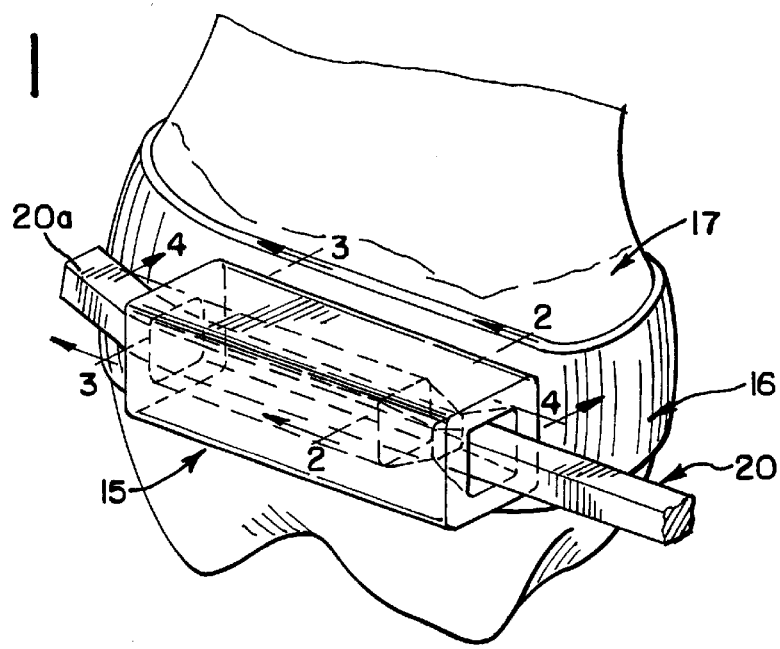
FIG. 1 is a perspective view of the improved buccal tube according to the invention mounted on a band carried on a tooth and showing the interior of the tube in phantom and a fragmentary archwire in place.
Figure 2:
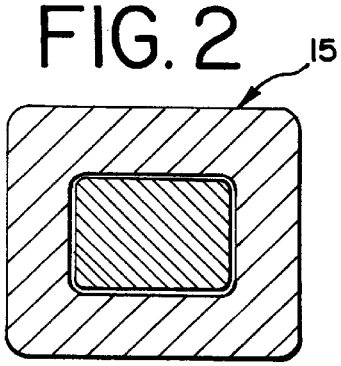
FIG. 2 is a transverse sectional view taken substantially along line 2—2 of FIG. 1.

Referring now to the drawings, and particularly the embodiment of FIGS. 1 to 5, a low friction orthodontic appliance in the form of a one-piece buccal tube, generally indicated by the numeral 15, is illustrated as being suitably mounted on a band 16 that is in turn adhesively secured to a tooth 17. It can be appreciated that the tube 15 may be secured in any suitable way to the band 16 and that both the tube and the band would be of a suitable metal. Thus, the tube may be suitably soldered and/or braised to the band prior to the mounting of the band and tube onto the tooth. It should also be appreciated the tube may be mounted on a bonding base and bonded to a tooth. The tooth 17 is shown as a molar and in the illustration would be an upper right molar and which would serve as the anchor for the distal end of an archwire 20. It would be appreciated that similarly the other end of the archwire would be anchored in a buccal tube usually mounted on the opposing molar on the left side.

It should also be appreciated that the archwire 20 would be rectangular in configuration so that it can provide a torquing force to the tooth by virtue of the control feature embodied in the tube as described below. Any suitable type of rectangular or square archwire may be used with the tube of the present invention. In this respect, the archwire could be metal, plastic or fiberglass, although preferably it is metal. Similarly, the tube may be metal, plastic or ceramic, but preferably metal such as stainless steel. Further, any suitable size of archwire may be used as long as the control portion of the tube is appropriately sized to closely receive the archwire. In this illustration the distal end 20a of the archwire is bent so that retraction of the archwire mesially through the tube is inhibited.

The buccal tube 15 is rectangular in cross section, although it may take any desired cross-sectional shape. Like the archwire, the tube is preferably of a suitable metal such as stainless steel, although it could be plastic, ceramic or a combination of such materials.

The tube includes a lumen 22 extending mesially and distally through the tube having a control portion 24 at the mesial end and a relieved portion 26 at the distal end. While the control portion is sized slightly larger than the archwire such as to allow sliding movement therebetween, the relieved portion is substantially greater than the archwire to essentially eliminate friction between the archwire and the lumen. It should be appreciated, however, that the control portion could be disposed at the distal end and the relieved portion could be disposed at the mesial end. It is preferred that the control portion be disposed at the mesial end of the tube.

Figure 3:
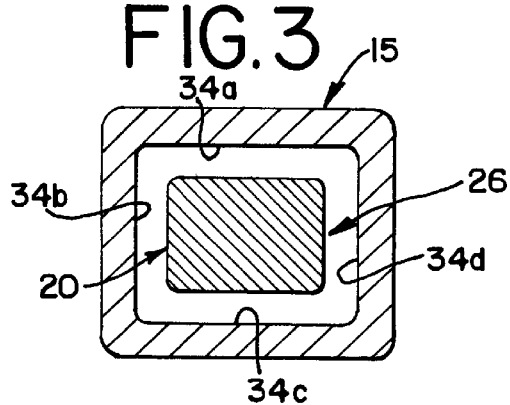
FIG. 3 is a transverse sectional view taken substantially along line 3—3 of FIG. 1.
Figure 4:
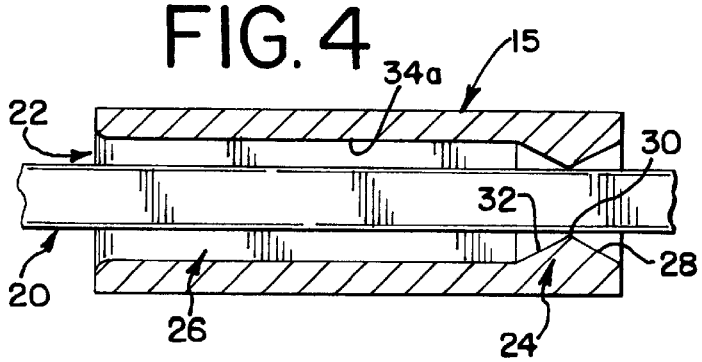
FIG. 4 is a longitudinal sectional view taken substantially along line 4—4 of FIG. 1 but showing the archwire in side elevation.
Figure 5:
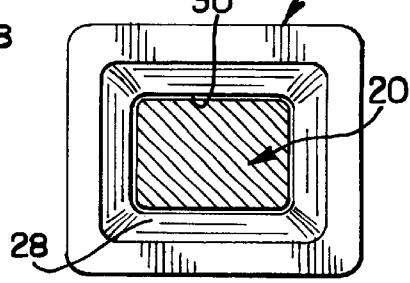
FIG. 5 is an elevational view of the mesial end of the tube in FIG. 1 and showing the archwire in cross section.

The control portion 24 is defined by an archwire engaging section 30, having on one side a mesial chamfer or flared section 28, and on the other side a distal chamfer or flared section 32. The mesial chamfer section 28 provides a guiding action to the archwire as it is initially inserted into the lumen of a tooth to guide the archwire through the engaging or contact section 30. The engaging section or control portion is sized slightly larger than the peripheral external dimensions of the archwire to effect torquing control between the archwire and the tube while allowing a sliding relation therebetween and of a rather narrow mesio-distal width such that sliding friction is minimized while maintaining torquing control. The distal chamfer section 32 opens to the relieved or relief portion 26 which preferably is sized substantially greater than the external cross-sectional dimension of the archwire such that the archwire will not normally engage more than one of the side walls of the relief portion. The relieved portion includes walls 34a, 34b, 34c and 34d providing potentially equal spacing around the archwire, as seen in FIG. 3, when the archwire is centered in the relieved portion, thereby providing clearance at the entire periphery of the archwire. Preferably, the length of the relieved portion extends at least eighty percent of the length of the tube. However, the length may be in the range of fifty to ninety-nine percent of the length of the tube. Likewise, the mesial-distal width of the control portion may be in the range of one to fifty percent of the length of the tube.

The distal chamfer section 32 facilitates the withdrawal of the archwire during the treatment of a patient and where the distal end of the archwire may be slightly bent from the axis of the archwire.

Even though the engagement section 30 is illustrated to have a generally edge contact with the archwire, it will be appreciated that the longitudinal length of the engagement section may be slightly greater than the edge contact as generally illustrated in the embodiment of FIGS. 6 to 11. However, it is preferable that the engagement contact with the archwire be a substantially smooth surface to minimize the friction between the archwire and tube while providing torquing control.

Referring now to the convertible buccal tube embodiment of FIGS. 6 to 11, it will be appreciated that the invention may be embodied in such a tube, wherein at least three sides of the archwire may be spaced from the walls of the lumen in order to reduce friction in such a convertible buccal tube. A convertible cap functions as one wall of the tube and is selectively removable in order to form an open archwire receiving slot. Tie wings are provided for receiving a ligature in order to retain the archwire on the tube when in its bracket form. It will be appreciated that a convertible buccal tube will be used wherein it is first desired to merely anchor the archwire and later have the appliance serve as an edgewise bracket in the more advanced stages of treatment.

The convertible buccal tube of the invention is generally designated by the numeral 40 and includes a body 41 having upper and lower tie wings 42 and 43. A convertible cap 45 which when secured to the body 41 of the tube coacts with an archwire slot 48 to define a lumen 50. Thus, the convertible tube is a two-piece unit although, when assembled, it is in the form of a one-piece unit as the convertible cap is removably secured in place. A distally directed hook 52 is shown on the tube in FIG. 6, while the remaining FIGS. 7 to 11 are shown without a hook for simplicity purposes. It can be appreciated that any type of hook may be provided on a tie wing if desired, and it also may be removable if not needed. Further the upper tie wing 42 is shown as a twin tie wing, while the lower tie wing is shown as a single tie wing, and it can be appreciated that both the upper and lower tie wings may be twins or they may be singles.

The convertible cap 45 is rectangular in configuration and when mounted on the tube body 41 fits in upper and lower notches 54 and 55. The cap may be suitably secured in place by welding or soldering but removable during treatment in order to convert the buccal tube to a bracket. The cap is illustrated in mounted position on the tube body 41 in FIGS. 7, 8, 9 and 10, and in this position it defines the lumen 50 which includes a control portion 58 at the mesial end of the tube and a relief portion 59 distal to the control portion. The control portion 58 is defined by horizontal upper and lower parallel opposed ridges 58a and 58b and an interconnecting vertically extending ridge 58c. The fourth side of the control portion is defined by the convertible cap 45. Inasmuch as the buccal face of the archwire 20 may at least sometimes lay against the inner surface of the convertible cap 45, such as particularly illustrated in FIG. 8, it will be appreciated that the relief portion may only extend around three sides of the wire as shown in FIGS. 9 and 10. The relieved portion is defined by upper and lower opposed walls 50a and 50b and a vertical side wall 50c. The relieved portion is closed by the convertible cap 45. Preferably, the relieved portion extends at least eighty percent of the length of the lumen, although it may be fifty to ninety-nine percent of the length of the lumen, as in the first embodiment. It will also be appreciated that the control portion, while illustrated in the embodiment of FIGS. 6 to 10 at the mesial end of the tube, could be positioned at the distal end of the tube, as explained relative to that possibility with the embodiment of FIGS. 1 to 5. The width of the control portion surfaces 58a, 58b and 58c may vary although it is critical that the surfaces are such as to apply a torquing force between the tube and the archwire. Because of the reduced length of the engagement between the archwire and the control portion, the friction between the archwire and the tube is reduced to the minimum, thereby enhancing the treatment program of a patient. One example of a convertible tube having a length of 0.175 inch, and a mesiodistal contact edge width in the control portion of 0.005 inch, would cause the relieved portion to be about ninety-seven percent of the tube length.

Once the convertible buccal tube has served its purpose as a buccal tube and there is a need to use it as a bracket, the convertible cap 45 is removed so as to provide a horizontal or buccally opening archwire slot and where the archwire then is retained in the slot by means of a ligature, such as the elastic ligature 62 shown in FIG. 11. The control portion continues to operate to provide a torquing relationship between the bracket and the archwire and also to reduce the friction between the archwire and the tube during the treatment phase.

Accordingly, the convertible buccal tube of the embodiment of FIGS. 6 to 11 is capable of not only serving as a buccal tube with reduced friction but also as a bracket with reduced friction.

It will be understood that modifications and variations may be effected without departing from the scope of the novel concepts of the present invention, but it is understood that this application is to be limited only by the scope of the appended claims.

The invention is hereby claimed as follows:

1. A low friction orthodontic torquing appliance adapted to be secured to a tooth comprising:
   a lumen extending mesial-distally therethrough for receiving the distal end of an archwire,
   said lumen having a mesial end and a distal end,
   said lumen including a control portion at the mesial end of the appliance,
   said control portion defining a close fit between the appliance and archwire such that torque clan be applied between the wire and appliance,
   and a relieved portion at the distal end of the appliance providing clearance between at least three sides and corners of the archwire and the appliance thereby reducing the sliding friction between the appliance and the archwire.

2. The appliance of claim 1, wherein said relieved portion provides clearance at the entire periphery of the archwire.

3. The appliance of claim 1, wherein the length of the relieved portion is about 80 percent of the length of the appliance.

4. The appliance of claim 1, wherein the length of the relieved portion is in the range of fifty to ninety-nine percent of the length of the appliance.

5. The appliance of claim 1, wherein the mesial-distal width of the control portion is one to fifty percent of the length of the appliance.

6. The appliance of claim 1, wherein the control portion is rectangularly shaped.

7. The appliance of claim 1, wherein the control portion is square shaped.

8. The appliance of claim 1, wherein the control portion includes a potentially continuous contact surface for engagement with the archwire.

9. The appliance of claim 1, wherein the control area includes means for producing labiolingual and occlusogingival control over the archwire.

10. The appliance of claim 1, wherein the appliance is in the form of a one-piece buccal tube.

11. The appliance of claim 1, wherein the appliance includes means for converting the torquing appliance to a bracket.

12. A low friction one-piece buccal tube adapted to be secured to a tooth comprising:
    a lumen extending mesial-distally therethrough for receiving the distal end of an archwire,
    said lumen having a mesial end and a distal end,
    said lumen including a control portion at the mesial end of the tube,
    said control portion defining a close fit between the tube and archwire such that torque can be applied between the wire and tube,
    and means in the lumen for reducing the sliding friction between the archwire and the tube including a relief area around at least three sides and corners of the archwire.

13. A low friction convertible buccal tube comprising:
    a lumen extending mesial-distally therethrough for receiving the distal end of an archwire,
    said lumen having a mesial end and a distal end,
    said lumen including a control portion at the mesial end of the tube and a relief portion at the other end of the tube,
    said control portion defining a close fit between the tube and archwire such that torque can be applied between the wire and tube and said relief portion reducing the sliding friction between the archwire and the tube and providing clearance around at least three sides and corners of the archwire,
    tie wings, and a removable convertible cap for converting the tube into a bracket having a buccal opening for receiving an archwire retainable by a ligature over the tie wings.

14. The buccal tube of claim 13, wherein the mesial-distal width of the control portion is in the range of one to fifty percent of the length of the tube.

* * * * *